United States Patent [19]
Mitchell et al.

[11] Patent Number: 5,318,028
[45] Date of Patent: Jun. 7, 1994

[54] HIGH RESOLUTION ULTRASOUND MAMMOGRAPHY SYSTEM AND BOUNDARY ARRAY SCANNER THEREFOR

[75] Inventors: Bruce C. Mitchell, Ellicott City; Leslie M. James, Severna Park, both of Md.

[73] Assignee: Westinghouse Electric Corporation, Pittsburgh, Pa.

[21] Appl. No.: 72,810

[22] Filed: Jun. 7, 1993

[51] Int. Cl.$^5$ .............................................. A61B 8/00
[52] U.S. Cl. ............................................... 128/660.08
[58] Field of Search ...................... 128/660.07, 660.08, 128/661.1, 915, 916; 73/626

[56] References Cited

U.S. PATENT DOCUMENTS

| | | | |
|---|---|---|---|
| 4,434,799 | 3/1984 | Taenzer | 128/915 X |
| 4,509,368 | 4/1985 | Whiting et al. | 128/915 X |
| 4,570,488 | 2/1986 | Miwa et al. | 128/916 X |

OTHER PUBLICATIONS

"Ultrasound Mammography", ed. Pat Harper, M.D.; (University Park Press, Baltimore), pp. 2-20.
Harper et al., "Ultrasound Breast Imaging–The Method of Choice for Examining the Young Patient", Ultrasound in Med. & Biol., vol. 7, (1981), pp. 231-237.
Leucht et al. "Sonographic Demonstration and Evaluation of Microcalifications in the Breast", Breast Dis, 5, (1992), pp. 105-123).
Bassett et al., "Usefulness of Mammography and Sonography in Women Less than 35 Years of Age", Radiology, vol. 180, No. 3, (1991), pp. 831-835.
Bassett et al., "Breast Sonography", Review Article, AJR, 156, (Mar. 1991), pp. 449-455.
E. A. Sickles, "Imaging Techniques other than Mammography for the Detection and Diagnosis of Breast Cancer"; Cancer Research, vol. 119 (Springer-Verlag, Berlin, 1990), pp. 127-135.
Bassett et al. "Automated and Hand-held Breast US: Effect on Patient Management", Radiology, vol. 165, No. 1, (1987), pp. 103-108.
Elizabeth Kelly-Fry, "Breast Cancer Screening for Younger United States Women", presented at Indiana Univ. Med. Ctr., Dept. of Radiology, Indianapolis, Ind. (ed. by J. Jellins and T. Kobayashi; (John Wiley & Sons, Inc., 1983), pp. 265-273.

*Primary Examiner*—Francis Jaworski

[57] ABSTRACT

A synthetic four sides boundary scanner array is provided for an ultrasound mammography system. Projector and hydrophone elements are alternately disposed on the four array sides for stepped movement along the four sides during a scan of a breast volume. Electric signals generated by the hydrophone elements are processed to provide image data for displaying the breast volume. A breast scan is performed within the time between a patient's heartbeats.

17 Claims, 5 Drawing Sheets

HIGH RESOLUTION ULTRASOUND MAMMOGRAPHY SYSTEM AND BOUNDARY ARRAY SCANNER THEREFOR

BACKGROUND OF THE INVENTION

The present invention relates to mammography systems and more particularly to ultrasound mammography systems and ultrasonic scanners therefor.

Mammography is a generic term that is used herein to refer to various techniques by which breast imaging may be performed, normally for medical diagnostic purposes. Elsewhere, however, the term "mammography" has been used and continues to be used in a more limited sense to mean X-ray breast imaging, since X-ray procedures have generally provided the best imaging results to date and, accordingly, have been the most widely used procedures.

While X-ray mammography has been successfully and widely used for breast cancer detection, there are nonetheless disadvantages associated with it. First, the X-ray mammography procedure creates a hazard of radiation exposure which desirably is to be avoided if alternatives are available.

In addition, the X-ray mammography procedure typically is constrained by an equipment capability limit on the depth to which effective breast imaging can be achieved. As a result, effective breast imaging with X-ray mammography often requires breast compression procedures that are usually painful.

X-ray mammography has also been limited in its effectiveness for younger female patients. As set forth in an article entitled "Ultrasound Breast Imaging—The Method of Choice for Examining the Young Patient" and published by Patricia Harper et al. in *Ultrasound in Med. & Biol* in 1981 in Great Britain, radiographic imaging has not significantly improved the accuracy of diagnosis of masses present in the dense breasts of young women. Thus, as indicated in this article, breasts of a majority of patients under 30 years of age have a predominance of glandular tissue and are usually characterized, for purposes of radiographic imaging, as "dense breasts". The term "dense breast", as used in X-ray mammography, refers to a breast which contains a predominance of dense tissue, such as glandular tissue, and, at the kilovoltages used in mammography, shows poor contrast between the predominant tissue and other breast tissues, either normal or pathological.

X-ray mammography is also somewhat limited from the standpoint of image dimensions. Thus, in the X-ray mammography procedure, a silhouette of a whole three-dimensional breast region is projected on a two-dimensional plate. To obtain an image along another dimension, another image must be taken from another angle.

Microcalcifications in breast tissue are known to be a possible early precursor to a malignant tumor. Accordingly, it has been determined that, to be diagnostically effective, mammography procedures should have sufficiently high resolution to detect microcalcifications 100 microns (millionths of a meter) or less in size. X-ray mammography has been widely accepted largely because it has the capability of detecting microcalcifications as small as 50 to 75 microns, whereas other procedures have lacked such high resolution.

Various other potential mammography procedures have been determined to hold little promise for clinical use as described in a 1990 article entitled "Imaging Techniques Other than Mammography for the Detection and Diagnosis of Breast Cancer" and published by E. A. Sickles in Recent Results in Cancer Research. Thus, computerized tomography (CT) scanning with the use of dedicated breast scanners and whole body scanners have involved high examination cost, intravenous iodide administration with radiation doses higher than those used for X-ray mammography, and difficulty of interpretation.

As further indicated in the 1990 article, transillumination procedures are limited by a fundamental problem of light scattering. Magnetic resonance imaging has been indicated as holding some promise as a diagnostic test to complement mammography and physical examination for already detected lesions. Specifically, magnetic resonance may be useful in distinguishing benign from malignant solid masses with sufficient accuracy so that biopsy of many of the benign lesions can be avoided.

By far, an alternative technology that has held the greatest hope for improved mammography has been the use of sonographic procedures as indicated by much of the literature published over the last ten years or so. An article entitled "Ultrasound Mammography" and published by Pat Harper, M.D. in University Park Press in Baltimore provides some description of the development of ultrasound breast examination procedures and apparatus from the 1960s through the 1980s. Harper concludes that currently (at that time) there is an increased willingness to recognize the benefits of ultrasound as an adjunctive technique to X-ray mammography and under certain precisely specified circumstances as a sole examination modality.

In a 1983 article entitled "Breast Cancer Screening for Younger United States Women" and published by Elizabeth Kelly Fry in 1981 in Ultrasonic Examination of the Breast (John Wiley & Sons), it is indicated that ultrasound visualization had been used in Japan in ongoing investigations for breast cancer screening with instruments similar to those used for examination of symptomatic patients. The Fry article concludes that the primary breast examination technique available to United States asymptomatic women under the age of 35 is manual palpation, while limited use of x-ray mammography has been recommended for women in the age range of 35–50.

Fry further indicates that X-ray mammography is not an adequate detection technique for women between 35 and 50 who have dense (i.e., non-fatty) breasts, so that some of this age group are dependent on manual palpation. Since palpation does not generally detect tumors less than 1 cm, it has limited value from the viewpoint of early detection. Efforts should be made to provide a non-ionizing screening technique for examination of adult women below the age of 50, with particular emphasis given to women under age 35.

Fry recommends that intensive efforts be placed, in the United States, on improving ultrasound instrumentation so that it is capable of detecting minimal cancers in that population of women where such early cancers are most likely to be found, namely, the younger woman.

In the 1990 Sickles article, the major clinical role for breast ultrasound is to differentiate cysts from solid masses. Further, the greatest usefulness of sonography occurs when cyst-solid differentiation is needed for nonpalpable masses for which aspiration is impractical (Kopans 1987; Sickles et al. 1984). This circumstance applies when a noncalcified nonspiculated mass is detected by mammography alone. Similarly, in a 1991 article entitled "Breast Sonography" and published by Lawrence W. Bassett and Carolyn Kimme-Smith in AJR 156, it is concluded that sonographic equipment for breast imaging has continued to improve, and the role of breast sonography has evolved to that of an indispensable adjunct to (x-ray) mammography. Breast sonography, using the hardware available today, is not useful for screening for breast cancer in any age group. Its main use is for the differentiation of cystic versus solid palpable and x-ray mammographically visible masses.

A 1991 article entitled "Usefulness of Mammography and Sonography in Women Less than 35 Years of Age" and published by L. W. Bassett, M.D. et al. in Radiology presents further discussion of the effectiveness of the use of X-ray mammography and breast sonography for younger women. It concludes that mammography is apparently less effective in the evaluation of the radiodense breasts of younger women than of the less radiodense breasts of older women.

In Radiology (1987), an article entitled "Automated and Hand-held Breast US: Effect on Patient Management" and published by L. W. Bassett, M.D. et al. in Radiology, it is indicated that automated ultrasound units, designed for examination of the breasts of symptomatic patients, have been advocated as a potential screening device for breast cancer, with detection rates reportedly approaching those of X-ray mammography. Some investigators, however, have reported significant numbers of cancers detected with mammography but undetected with automated ultrasound. Recently, it has been emphasized that identification of benign breast lesions with ultrasound in asymptomatic patients should not be considered a useful effect because it often leads to unnecessary biopsies. However, ultrasound has been shown to be useful as a complement to X-ray mammography in specific clinical situations. Its most widely accepted current role is in the differentiation of cystic from solid masses found by palpation or on X-ray mammograms. The results of a patient study show that although ultrasound, using currently available hardware, cannot replace X-ray mammography in breast cancer screening, it may play an important role in the evaluation of selected patients.

A more recent 1992 article entitled "Sonographic Demonstration and Evaluation of Microcalcifications in the Breast" and published by W. J. Leucht, M.D. et al in Breast Dis concludes that investigation has shown that sonographic demonstration of microcalcification correlates (as tissue alterations and as visualized calcium particles) is possible. It is further indicated that routine preoperative mammary sonography is regarded as useful, as it can help determine the correct operative procedure. Thus, radiographically detected microcalcifications suggestive of malignancy may be backed up by a sonographic microcalcification correlate predictive of malignancy.

The rapidly increasing interest in very high resolution ultrasonic mammography as represented by the above sampling of articles, is a response to the pain and radiation hazard problems from X-ray mammography and a desire to find a more effective tumor detector. To achieve acoustic resolution comparable to X-ray resolution requires minimizing the image distortion problems arising from the heterogeneity in the breast. Heterogeneity results in variable acoustic path lengths and acoustic path loss variation. Cost of equipment is also a major factor. An acoustic scanning method must also eliminate body movement effects during scanning. In general, these problem areas may be minimized by using an ultrasound mammography system with a scanner having the smallest possible physical array with the lowest element spot count.

The acoustic absorption coefficient of breast tissue increases rapidly with frequency. Therefore, sufficient breast penetration requires use of a relatively low frequency and a large transducer array. For example, to achieve 100 $\mu$m resolution at the chest wall 6 inches below the array requires an 8 inch wide real array, operating at 10 mHz. The ray paths from the focus point to different points on this array can travel through different path lengths and tissue types. The resulting signal amplitude and phase distortion across the scanner array can significantly degrade resolution. A fully populated square scanner array of this size would have $7.1 \times 10^6$ element spots. Fabrication of such a scanner array and its associated electronics is presently beyond the state of the art.

The required high element spot count also produces an excessive computation problem in an ultrasound mammography system. A typical breast volume is $8.2 \times 10^{-4}$ m$^3$. An achievable acoustic resolution volume is $2.5 \times 10^{-12}$ m$^3$ which gives a breast volume of $3.28 \times 10^8$ resolution cells. The scanner array operates deep in the near field so that the processing load is proportional to the product of the array element spot count and the resolution cell count. The fully populated 8 inch square real scanner array above requires approximately $2.3 \times 10^{15}$ real multiplies to image the breast volume. A typical clinic load is 100 breasts per day so that $1.1 \times 10^{13}$ real multiplies/second processing rate would be required. This is several orders of magnitude beyond practical machine capability.

A Mill's Cross array reduces the element spot count by a factor of N/2 where N is the element spot count along one edge of the square array. For the example, the real multiply rate is reduced to $8.3 \times 10^9$ multiplies per second which is an achievable value. The maximum real Mill's Cross array dimensions are the same as the filled array, however, so the acoustic path distortion problems remain.

One dimension of the Mill's Cross beam resolution is produced by the projector beam. The depth of field about the focus range for this beam is very small when applied to the ultrasonic mammography problem. This requires the projector to be refocused for typically 370 depth planes in addition to its typical range of 1270 lateral positions. The time to scan a breast is approximately 35 seconds. On a scale of 100 micron resolution, the breast moves excessively in this time period.

The final problem with the real Mill's Cross array is fabricating its two eight inch real arrays of approximately 2667 elements each. This is beyond the state of the art.

Implementing the Mill's Cross array by scanning a projector element to form a synthetic array and collecting the data with a real hydrophone array reduces scan time computational load sufficiently. It does not reduce array size sufficiently, however, nor does it avoid the problem of fabricating the hydrophone array.

The hydrophone array complexity can be reduced by scanning a single hydrophone element to form the hydrophone array synthetically. The hydrophone element is swept the length of its "array" for each transmission of the projector at spots along its "array" length. This requires approximately 24 seconds to scan a breast, which is excessive.

In a copending patent application Ser. No. 08/072,806 entitled "Sonar System Employing Synthetic Orthogonal Array" and filed by B. Mitchell and G. Greene, a synthetic Mill's Cross array is implemented with paired elements in a manner which reduces the typical breast scan time to 1.1 seconds. The beam sidelobes are low enough so contrast is acceptable under some conditions but the scan time is still excessive to avoid image degradation from body movement.

A single element may be scanned in a circle over the image region to form a synthetic circular array used in the spotlight mode. A breast can be scanned in 0.48 seconds which is acceptable. The excessive sidelobe response results in insufficient contrast.

A single element may also be used to form a square synthetic array. The typical scan time of 0.45 seconds for a breast is acceptable. The high sidelobe problem, which results in low contrast, is more severe than the circular synthetic array.

While interest in ultrasound mammography has been high, the scanner resolution and fabricability problems outlined above have been a major deterrent to development of ultrasound mammography toward becoming a preferable alternative to X-ray mammography.

SUMMARY OF THE INVENTION

The present invention is directed to providing improved breast cancer detection by means of an ultrasound mammography system and an ultrasound scanner therefor that enable essentially painless, radiation-free breast imaging to be performed reliably with sufficiently high resolution that microcalcifications smaller than 100 microns can be detected. Thus, an ultrasound mammography system comprises a synthetic scanner array having a boundary formed by predetermined sides each having successive position spots with predetermined spacing therebetween.

Means are provided for projecting acoustic signals into a breast volume to be scanned and for receiving reflected signals from the scanned breast volume. The projecting means and the receiving means are disposed at predetermined locations along the scanner array sides, and means are provided for stepping the projecting means and the receiving means from spot to spot along the array sides to enable a breast volume scan to be performed. The projecting means are energized to transmit an acoustic signal into the breast volume from each spot to which the projecting means is stepped.

Electric signals generated by the receiving means are processed in response to reflected acoustic signals received at each spot to which the receiving means is stepped thereby to provide image data for the scanned breast volume. Means are provided for controlling the rate at which the stepping and energizing means are operated so that sufficient return data is generated to enable a breast scan normally to be executed in less time than the time between heartbeats of a patient. The image data is processed for display.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are incorporated in and constitute a part of this specification, illustrate a preferred embodiment of the invention and together with the description provide an explanation of the objects, advantages and principles of the invention. In the drawings.

DESCRIPTION OF THE INVENTION

Figure 1:
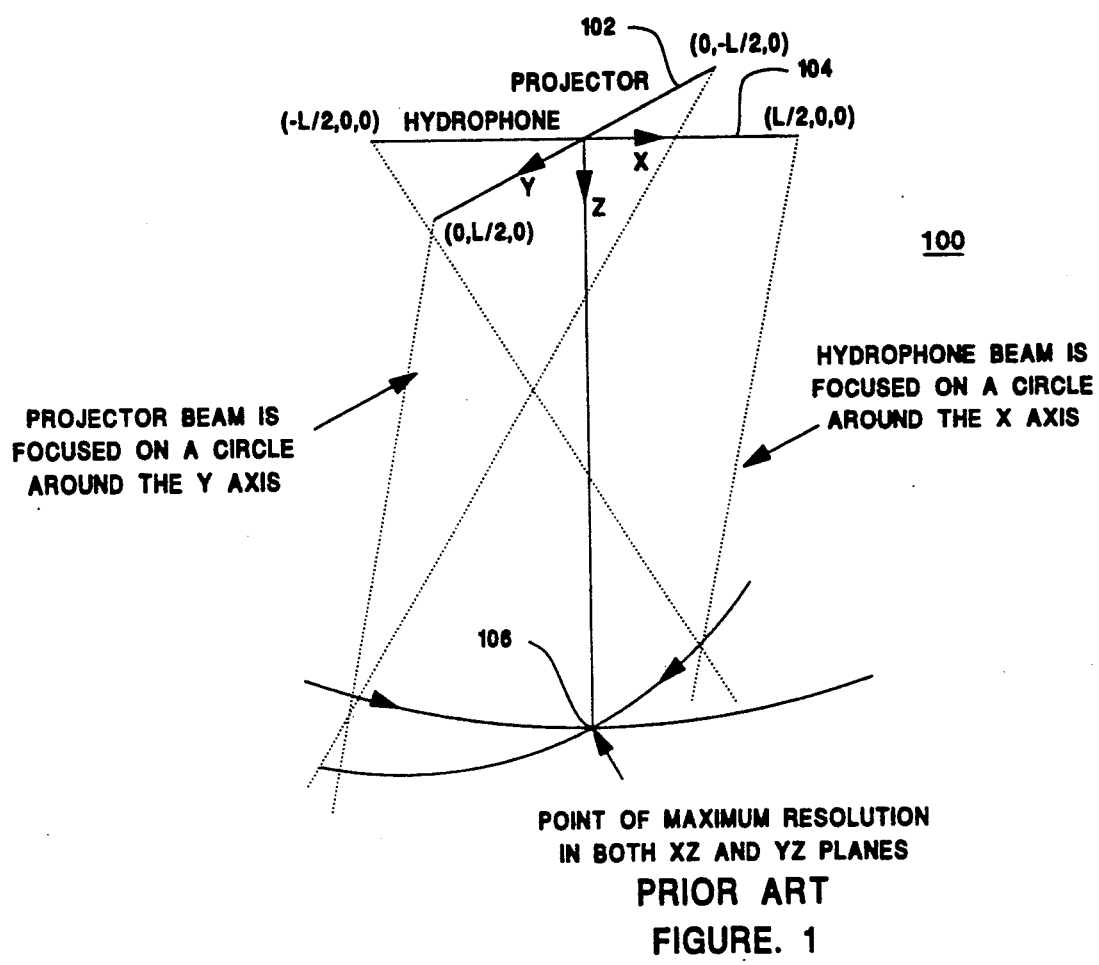
FIG. 1 is a schematic diagram of a prior art Mill's Cross transducer array.

In FIG. 1, there is shown a prior art Mill's Cross scanner array 100 which is formed from two transducer line arrays. The Mill's Cross is an array concept that has been employed in sonar technology for many years.

SCANNER ARRAYS—PRIOR ART

A limited description of the prior art Mill's Cross array 100 is provided herein to facilitate an understanding of the invention.

The prior art scanner array 100 includes orthogonal projector and hydrophone axes 102 and 104. Tiny acoustic projector elements (not indicated) are positioned along the Y-axis 102. Tiny hydrophone receiving elements (not indicated) are positioned along the X-axis 104.

The projector elements transmit an acoustic beam that is focused on a circle around the Y-axis. The hydrophone elements receive an acoustic reflection beam focused from a circle around the X-axis. A point of maximum resolution in both the XZ and YZ planes is indicated by the reference character 106.

Acoustic scanning of a volume to locate targets in three dimensions requires a scanner array having at least two dimensions with N elements along each dimension. As compared to a "full" two-dimensional array, the prior art Mill's Cross array 100 reduces the required number of transducer elements to 2N from $N^2$. As indicated in the Background section hereof, the physical size of a real Mill's Cross array 100 and that of a filled two-dimensional array are the same. Further, the problem of fabricating the real Mill's Cross array 100 and its electronics for mammography system use is severe, if not impractical.

An improved sonographic system having a new paired element synthetic Mill's Cross array is more fully described in the aforementioned copending application Ser. No. 072,806.

Figure 2:
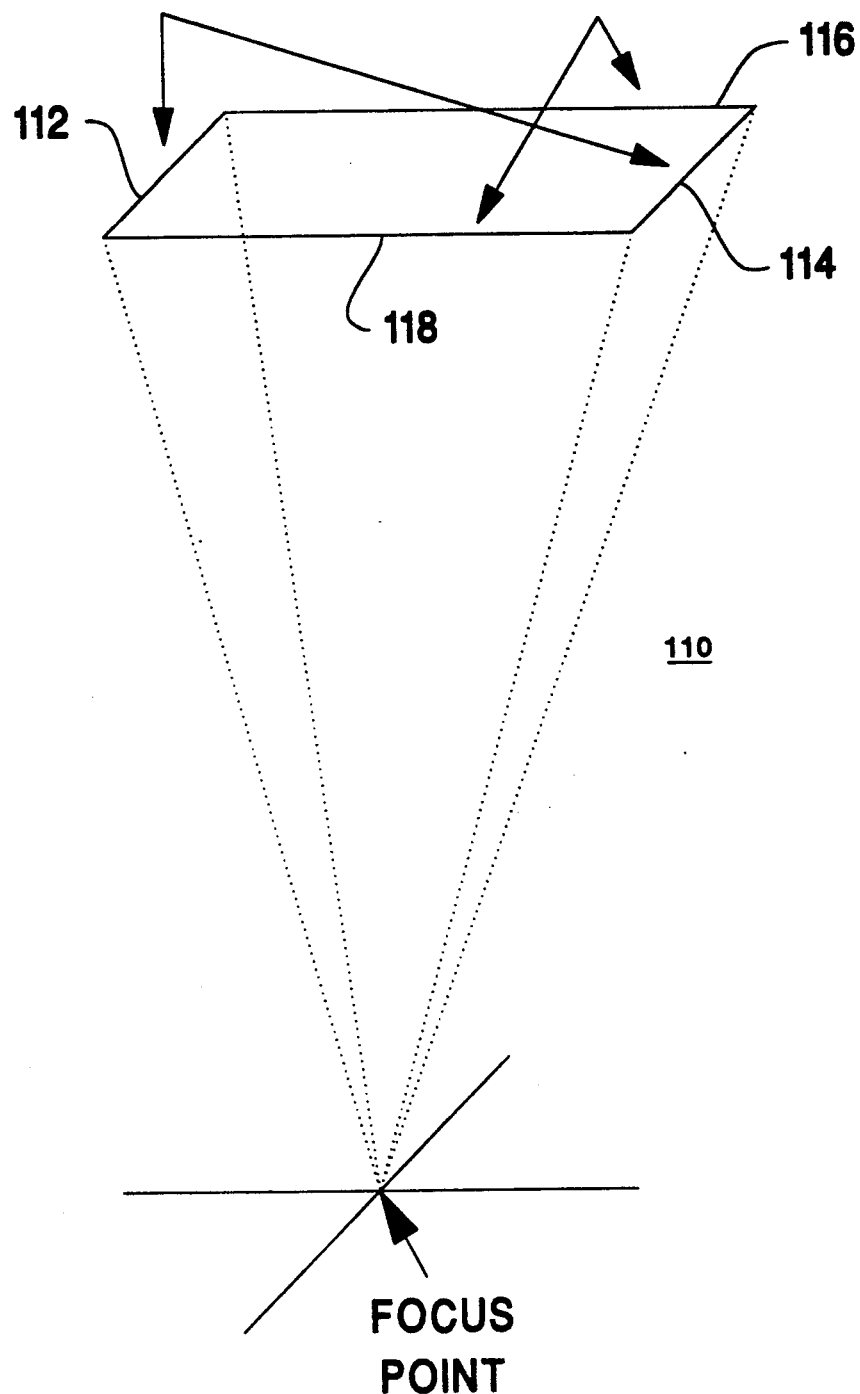
FIG. 2 is a schematic diagram of a prior art square boundary array transducer array.

A prior art real square boundary scanner array 110 is shown in FIG. 2. The boundary array 110 is, in effect, a combination an L-shaped half of each of two juxtaposed Mill's Cross arrays, and can achieve the image resolution of the Mill's Cross array 100 with half the array size.

As shown, four line arrays 112, 114, 116, and 118 form "boundary" sides for the prior art boundary scanner array 110. The opposite sides 110 and 112 have tiny projector transducer elements (not indicated) and the opposite sides 114 and 116 have tiny hydrophone transducer elements (not indicated).

In the prior art real square boundary array, hydrophone and projector element count is the same as that of a real Mill's Cross with the same resolution. The projector is two dimensional however. In ultrasonic mammography applications where the high range resolution requires time delay projector focusing in two dimensions, the scan time is nearly the square of the real Mill's Cross scan time discussed in the Background Section above. The real square boundary array, with its large arrays of tiny closely packed elements and long scan time, is impractical for mammography.

In accordance with the present invention, the arrangement of hydrophone and projector line arrays of a boundary array are implemented synthetically in a manner which minimizes complexity and scan time.

HIGH RESOLUTION SCANNER ARRAY FOR BREAST IMAGING IN ULTRASOUND MAMMOGRAPHY SYSTEMS OR FOR TARGET IMAGING IN OTHER SONOGRAPHIC SYSTEMS

The present invention provides an improved ultrasound mammography system that employs a synthetic array and boundary array concepts to achieve whole breast scanning with a significant reduction in scanner array size and transducer element count.

An example of the present preferred embodiment of the invention is illustrated in the accompanying drawings and will now be described in detail.

Figure 3:
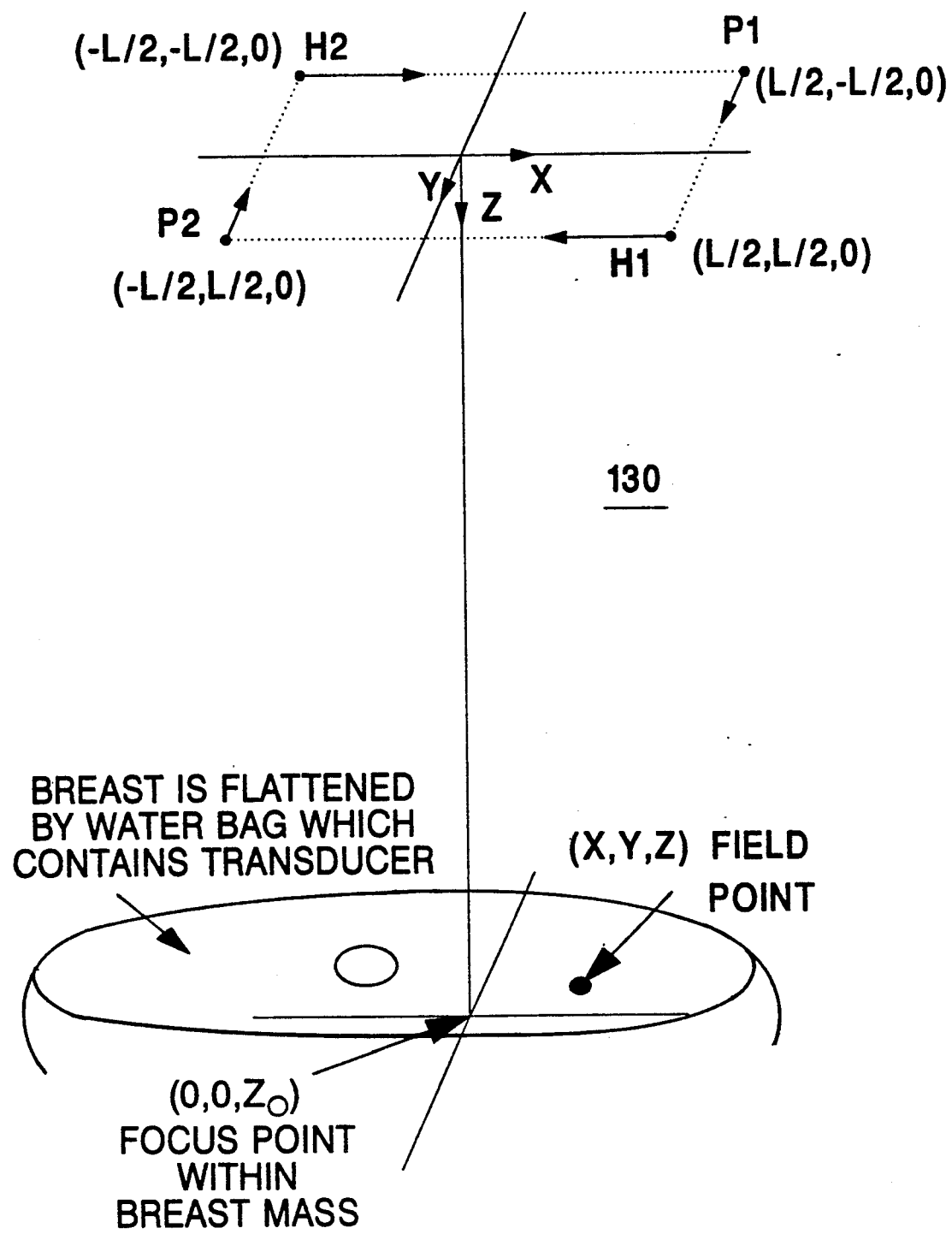
FIG. 3 is a schematic diagram of a synthetic, paired-element square, boundary transducer array employed in the system of FIG. 4.

A scanner array 130 arranged in accordance with the invention is illustrated in FIG. 3. A synthetic array structure reduces the array hardware complexity and resolves projector depth of field problems and has the overall dimensions of the boundary array. The physical element count is low which permits using a wide range of established element fabrication techniques. A body motion problem must be resolved, however, because an imaged volume must remain motionless during the period it is being scanned. In the specific mammographic case, the scan time must be less than the time between heartbeats, i.e., less than approximately 0.8 seconds.

Synthetic array methods have generally imitated airborne synthetic radar array technology. Of these "traditional" methods, the straight line, circular boundary, and square boundary are the most common. As noted in the Background Section above, the circle and square configurations have acceptable scan time but unacceptable sidelobe levels when scanning breasts. The scan time of 1.1 seconds for the synthetic paired element Mill's Cross (copending application WE 57713) is also excessive. With the incorporation of synthetic array methodology in the invention, the increased resolution results in a smaller array with acceptable scan time for mammography.

In accordance with the present invention, four transducer elements, H1, P1, H2, and P2, are scanned along coplanar straight lines as shown in FIG. 3, to form a four-sided and preferably a square scanner array 130. Elements P1 and P2 are projectors and elements H1 and H2 are hydrophones. The array dimensions are $L \times L$.

A rectangular boundary array (not shown) can also be formed if the beam resolution is different along the x axis relative to the y axis and if the number of element spots along the two axes are the same.

To form the synthetic boundary array 130, each projector or hydrophone element is placed on one of the boundary sides for stepped movement from spot to spot there along. The respective elements start at the respective corners of the square array 130. At the starting corner spot, P1 projector first transmits an acoustic pulse signal and backscatter acoustic data is collected by both hydrophones H1 and H2 and stored. Projector P2 then transmits an acoustic pulse signal and its backscatter data is collected by the projector H1 and H2 and stored.

After collection of the backscatter data, the projector elements are advanced along their lines to their next positions. These element spot positions are normally uniformly spaced but the spacing may be variable and the sequence of positions does not have to move the projectors uniformly from one end to the other of their respective lines. They must eventually scan the full line length however.

The hydrophones, H1 and H2 are repositioned along their lines when the projectors are repositioned. Their sequence of positions may be equally spaced or random and they may travel in the same direction from one end of the their lines to the other or they move randomly about. They must eventually scan their full line lengths however and each hydrophone element spot must be paired with a specific projector element spot.

The two basic methods of scanning—uniform or random—result in different characteristics in the array beam pattern. The method of processing the collected data also changes the beam pattern shape. The scanning and processing method is selected to match the application.

Maximum resolution is obtained by processing the data under programmed computer control as follows. The recorded data sample collected at the time required for the projected pulse to travel from P1 to the focus point and back to H1 is retrieved for each P1/H1 position pair. These samples are summed in complex form. This is repeated for the P1/H2, P2/H1, and P2/H2 combinations. The result is four complex numbers. The P1/H1 and P2/H2 numbers are added as are the P1/H2 and P2/H1 numbers. The magnitudes of the two resulting numbers are multiplied. The result is the beam response described by EQUATION (1). The logic needed to provide this data processing is embodied in a suitable programmed procedure that is executed by a block 37.

EQUATION 1: SYNTHETIC PAIRED ELEMENT BOUNDARY ARRAY BEAM RESPONSE $$f(x,y) = \frac{\sin(a)}{a} \frac{\sin(b)}{b}$$

where:

$$a = \frac{2\pi L(x - y)}{\lambda \left(\frac{L^2}{4} + Z_o^2\right)^{\frac{1}{2}}}$$

$$b = \frac{2\pi L(x - y)}{\lambda \left(\frac{L^2}{4} + Z_o^2\right)^{\frac{1}{2}}}$$

This beam pattern function has approximately four times the resolution of the synthetic Mill's Cross. Since it is produced by the multiplication of two subarray outputs which have fan beam responses, it is not applicable in a strong reverberant volume such as a human breast because of loss in contrast. It may be used where reverberation is limited to an adjacent surface or a limited number of scatterers in the volume.

For the mammogram application, the pseudorandomized scanning method causes the subarray response to drop rapidly with increasing distance from the focal point. EQUATION (1) correctly predicts beam resolution and the sidelobes are low enough to achieve good contrast. A beam resolution of 100 microns can be achieved at six inch range with a three inch square array operating at 10 mHz. The scan time, with overhead for randomizing the scan, is approximately 0.5 seconds. This is well under the limit imposed by heartbeats moving the body.

The second method of processing the data is to add the four complex numbers resulting from the four combinations from pairing P1, P2, H1, and H2. The resolution is half that achieved by multiplying the subarray outputs. With uniform element scanning, the highest sidelobes are down only six dB over extended distances. Using the pseudorandom scan method reduces the sidelobe to an acceptable level for mammography.

Figure 4:
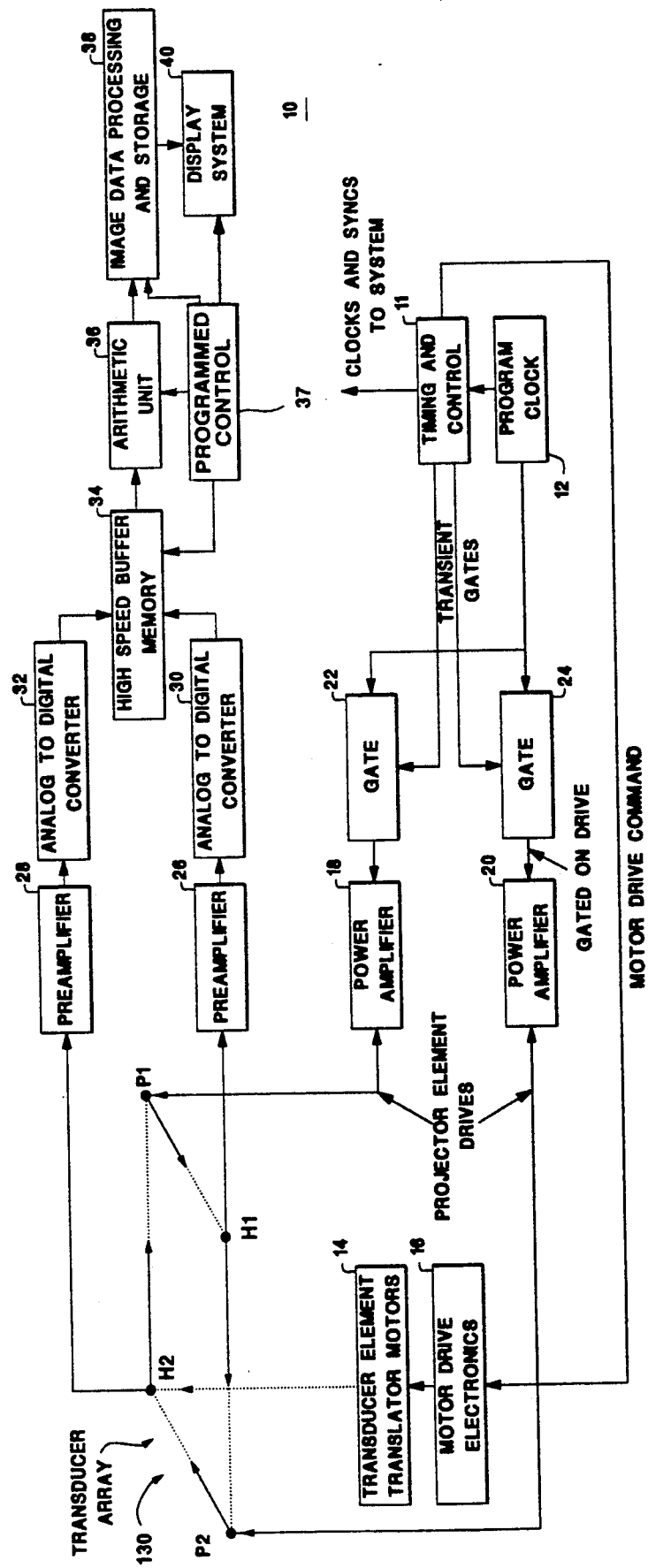
FIG. 4 is a block diagram of the preferred embodiment of a sonar transceiver which incorporates the transducer array in FIG. 3 to form a complete sonar mammorgraphy system.

A mammography system 10 shown in FIG. 4 includes the synthetic boundary array scanner 100 and other system elements to produce three-dimensional breast images from the scanner data in accordance with the above-described data processing procedures of the invention. The mammography system 10 is operated with the patient in a supine position.

A timing and control block 11 is employed in the mammography system 10 to generate command signals for the system circuitry. A precision clock 12 preferably operating with an accuracy of one part in $10^7$ parts provides an absolute time base during the time period of an array scan. A drift of less than 6 degrees over the span of a ping can be achieved if the clock 12 is embodied as a stable quartz crystal oscillator.

Respective translator motors 14 are provided for the transducer elements of the boundary scanner array 100, i.e., a separate motor 14 is provided for each transducer P1, P2, H1, and H2. Motor drive electronics 16 controls the energization of the motors 14 in response to command signals from the timing and control block 11.

Figure 5:
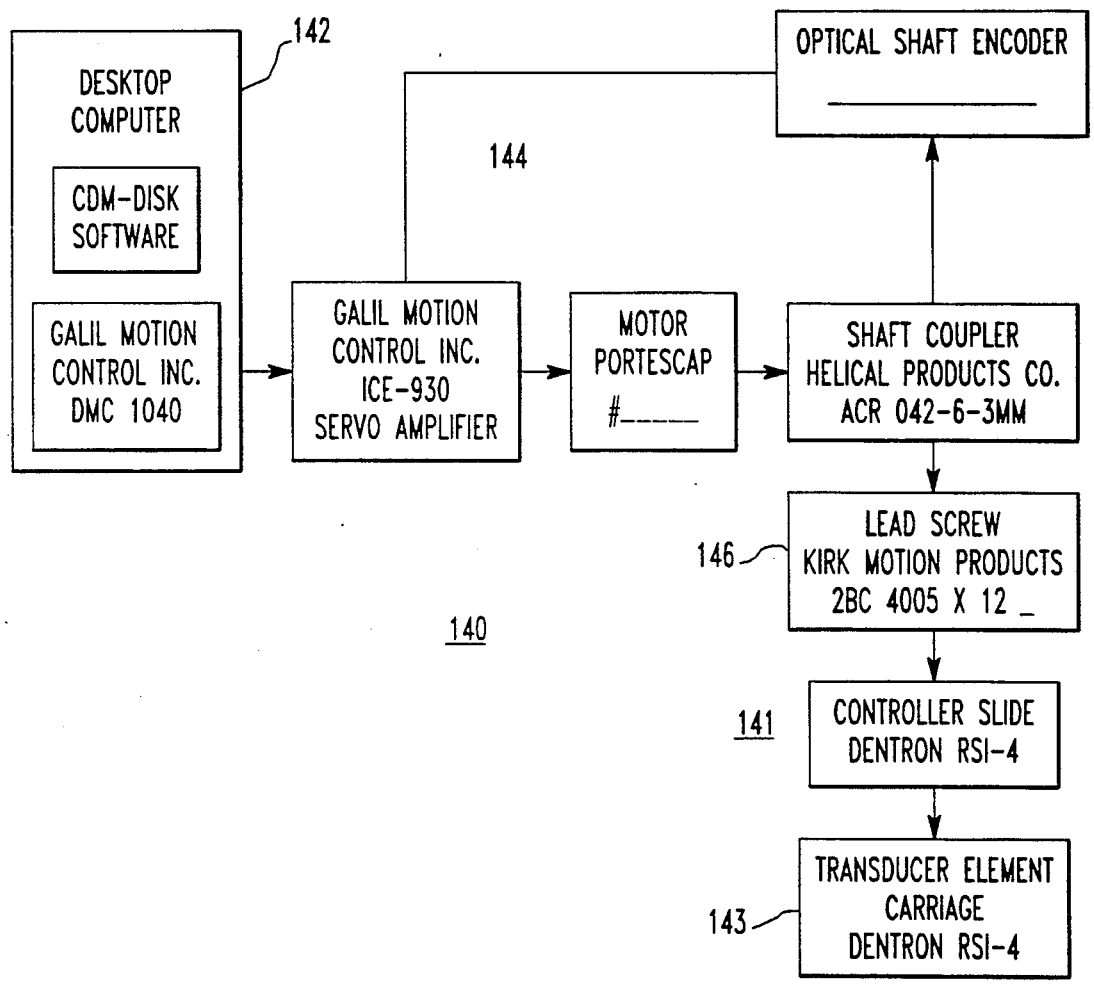
FIG. 5 is a block diagram of a transducer element scanner mechanism which uses commercial parts to implement and test the invention.

FIG. 5 is a block diagram illustrating a test system 140 for an element scanner mechanism 141 used to test the present invention. The system is controlled from a desktop computer 142 and uses commercially available components throughout. The mechanism required to move one element 143 is shown. Upon command from the system timing and control function, the computer 142 issues a position command to a servo system 144 which drives the element 143 to the correct position with a precision lead screw 146. The pattern of positions for the illustrated element 141 and the other three elements (not shown) is precomputed and stored in the computer 142. This system has been used to collect data from targets and process the data into images.

Respective power amplifiers 18 and 20 in FIG. 4 are connected to the projectors P1 and P2 to generate acoustic signals (pings) at the selected spot locations on the array sides. The timing and control block 11 applies command signals to respective gates 22 and 24 which, in turn, trigger the power amplifiers 18 and 20 to energize the projectors P1 and P2 and generate the pings from each spot location. Hydrophones H1 and H2 collect the acoustic signal backscatter from the P1 and P2 transmissions.

Preamplifiers 26 and 28 amplify and bandpass filter the two hydrophone output signals which are then converted to digital form by respective analog to digital converters 30 and 32. The digital signals are stored in a high speed buffer memory 34 until the scanning process is over. The form of the stored signal samples may be either complex or real. The complex form is preferred to simplify subsequent computations.

The signals are converted to complex form prior to computations made to form focused beams. This can be done with analog circuitry in the preamplifiers 26 and 28, by taking sequential samples 90 degrees apart in the converters 30 and 32, as preferred herein, by using coaxial cable delay lines or by subsequent digital filtering.

In a scan operation, the P1 gate 22 is first turned on and held on for one hold period (typically for 3 cycles of the sonar signal). The turn on point is precisely aligned with the sonar signal waveform, e.g. at a positive going zero crossing to maintain an accurate and repeatable time base throughout each ping cycle and from ping to ping. During the hold period, the projector P1 transmits an acoustic signal (pulse) and reflections are collected by the hydrophones H1 and H2 and converted to electric signals. In turn, the electric signals are amplified by the preamplifiers 26 and 28, converted to digital form by the converters 30 and 32 and stored in the memory 34.

Once the P1 data is collected, the P2 gate 24 is turned on and the above process is repeated so that a P2 ping is transmitted with reflection signals collected by the hydrophones H1 and H2 for conversion and storage. After the P2 data is collected, all of the transducers P1, P2, H1, and H2 are stepped to their next spots on the array sides and the described P1 and P2 ping procedure is repeated. The system 10 is stepped and pinged in this manner until the scan is completed, i.e. until the transducer elements have occupied each of their preselected positions over the full lengths of the boundary array sides.

The entire scan can be performed in approximately 0.5 seconds which means that the entire scan can be performed between a patient's heartbeats thereby making the system 10 applicable to mammography.

The reflection data collected from a scan provides a basis for imaging the breast volume scanned, i.e., the shape of tissue is determined by reflectivity characteristics. The nature of tissue is determined by the shape and relative contrast.

Microcalcifications tend to be more reflective and thus appear brighter in an output image, whereas tumors tend to be less reflective than surrounding tissue. The system 10 has the capability of detecting microcalcifications as small as 100 microns or less because the system resolution is 100 microns.

After the array scan is complete, the stored data is passed to an arithmetic unit 36 which computes the response at each point of interest in the target breast volume. The beam-formed data is then in a desired format and stored in block 38 where image processing is appropriately performed to format the data for any desired planar display by a display system 40.

In summary, the invention employs data scanning and processing that enables three dimensional ultrasound scanning to be achieved with very high resolution as contrasted with prior art ultrasound imaging systems which have been limited at best to a resolution of approximately one millimeter. In a mammography system, the invention enables breast imaging to be achieved reliably with a resolution better than 100 microns, and it does so safely without radiation exposure and without pain to the patient. The resolution of the system 10 results from a narrow beam spread at the focal point of 0.035 Degrees or finer. Thus, the invention provides a safe mammography system that is operable to screen effectively for breast microcalcifications and tumors and thus to function as a breast cancer screening system.

In summary of the operation of the invention, projector and hydrophone positions are paired to form synthetic orthogonal subarrays. Orthogonal fan beams are created with orientations determined by the manner in which the elements are paired to form the orthogonal synthetic subarrays. A square or rectangular synthetic boundary array is implemented by multiplying the outputs of the two orthogonal synthetic subarray outputs where the subarray fan beams are orthogonal or nearly orthogonal in the rectangular array case. A square or rectangular synthetic boundary array is also implemented by adding the outputs of the two orthogonal synthetic subarray outputs where the subarray beams are orthogonal or nearly orthogonal in the rectangular array case. The hydrophone or the projector element scan pattern can be pseudo-randomized to change the subarray fan beam into a beam shape with high resolution in all directions, thus achieving high signal to reverberation ratio or contrast in highly reverberant environments. Higher beam resolution is achieved for given sidelobe level, array dimensions and element spot count than with any other known transducer array technique.

In addition, the mammography system 10 achieves improved breast imaging performance with a scanner array that has manufacturing practicability and with an electronic data processing system that is commercially feasible. The volume of data samples per breast is less than 32 MBytes. The real multiply rate is approximately $3 \times 10^7$ per second to scan 100 breasts per day. This can be handled by two state of the art digital signal processor cards in a host desktop computer.

As a further advantage, a three dimensional image of the breast is produced, thereby facilitating three-dimensional viewing as compared to X-ray mammography. Thus, image processing software can slice the data along any desired plane to image the breast along that plane. This aids in classification of image features.

Generally, the invention can be implemented with square scanner arrays or with rectangular scanner arrays as long as the transducer element spot count is the same for each side of the boundary array. It is also noteworthy that the invention may be embodied in applications other than mammography. Thus, the invention may be used in any application where relative movement between the array and objects in the scanned volume is not excessive during the scan period. For example, a 30 inch square array can produce 0.5 inch by 0.5 inch by 0.5 inch resolution at 100 feet over a 60 degree angular sector. The scan time is 90 seconds.

The foregoing description of the preferred embodiment has been presented to illustrate the invention. It is not intended to be exhaustive or to limit the invention to the form disclosed. In applying the invention, modifications and variations can be made by those skilled in the pertaining art without departing from the scope and spirit of the invention. It is intended that the scope of the invention be defined by the claims appended hereto, and their equivalents.

We claim:

1. An ultrasound mammography system comprising:
   a synthetic scanner array having a boundary formed by predetermined sides each having successive position spots with predetermined spacing therebetween;
   means for projecting acoustic signals into a breast volume to be scanned;
   means for receiving reflected signals from within the breast volume to be scanned;
   the projecting means and the receiving means being disposed at predetermined locations along the scanner array sides;
   means for stepping the projecting means and receiving means from spot to spot along the array sides to enable a breast volume scan to be performed;
   means for energizing the projecting means to transmit an acoustic signal into the breast volume from each spot to which the projecting means is stepped;
   means for processing electric signals generated by the receiving means in response to reflected acoustic signals received at each spot to which the receiving means is stepped to generate an array beam response with a resolution of at least one hundred microns and thereby to provide image data for the scanned breast volume;
   means for controlling the rate at which the stepping and energizing means are operated so that return data is generated to enable a breast scan to be executed in less than one second which can be less than the time between heartbeats of a patient; and
   means for processing the image data for display.

2. The system of claim 1 wherein either the projecting means or the receiving means or both the projecting means and the receiving means are moved from spot to spot in a random manner such that each receiving means position is paired with a projecting means position with each boundary side being fully scanned.

3. The system of claim 2 wherein:
   the boundary array is a four-sided array;
   the projecting means includes first and second projectors;
   the receiving means includes first and second hydrophones;
   the projectors and hydrophones are alternately disposed on the respective array sides;
   the stepping means step the respective projectors and hydrophones from spot to spot in unison;
   the energizing means energizes the first and second projectors in succession to transmit successive first and second acoustic signals from respective projector spots in successive operating steps; and
   the processing means processes the electric signals generated by the first and second hydrophones in each operating step.

4. The system of claim 2 wherein the electric signals include respective outputs of the side arrays, and the electric signal processing means multiplies the array outputs.

5. The system of claim 1 wherein the electric signals include respective outputs of the array sides, and the electric signal processing means multiplies the array side outputs.

6. The system of claim 1 wherein the electric signals include respective outputs of the array sides, and the electric signal processing means adds the array side outputs.

7. The system of claim 1 wherein:
the boundary array is a four-sided array;
the projecting means include first and second projectors;
the receiving means includes first and second hydrophones;
the projectors and hydrophones being alternately disposed on the respective array sides;
the stepping means step the respective projectors and hydrophones from spot to spot in unison;
the energizing means energizes the first and second projectors in succession to transmit each first and second acoustic signals from respective projector spots in successive operating step; and
the processing means processes the electric signals generated by the first and second hydrophones in each operating step.

8. The system of claim 7 wherein the boundary array is a square array, and starting and ending points for each of the projectors and hydrophones are corner points of the array side on which the projector or hydrophone is located.

9. The system of claim 7 wherein the projector array sides and the hydrophone array sides all have the same number of stepping spots.

10. The system of claim 1 wherein the breast scan is enabled to be executed in less than 0.6 seconds.

11. A synthetic ultrasound scanner system comprising:
a boundary array formed by predetermined sides each having successive position spots with predetermined spacing therebetween;
means for projecting acoustic signals into a target volume to be scanned;
means for receiving reflected signals from within the target volume to be scanned;
the projecting means and the receiving means being disposed at predetermined locations along the scanner array sides;
means for stepping the projecting means and receiving means from spot to spot along the array sides to enable a target volume scan to be performed;
means for energizing the projecting means to transmit an acoustic signal into the target volume from each spot to which the projecting means is stepped;
means for processing electric signals generated by the receiving means in response to reflected acoustic signals received at each spot to which the receiving means is stepped to generate an array beam response with a resolution of at least one hundred microns and thereby to provide image data for the scanned target volume;
means for controlling the rate at which the stepping and energizing means are operated so that return data is generated to enable a target scan to be executed in a less than one second; and
means for processing the image data for display.

12. The system of claim 11 wherein:
the boundary array is a four-sided array;
the projecting means includes first and second projectors;
the receiving means includes first and second hydrophones;
the projectors and hydrophones are alternately disposed on the respective array sides;
the stepping means steps the respective projectors and hydrophones from spot to spot in unison;
the energizing means energizes the first and second projectors in succession to transmit successive first and second acoustic signals from respective projector spots in successive operating steps; and
the processing means processes the electric signals generated by the first and second hydrophones in each operating step.

13. The system of claim 11 wherein either the projecting means or the receiving means or both the projecting means and the receiving means are moved from spot to spot in a random manner such that each receiving means position is paired with a projecting means position with each boundary side being fully scanned.

14. The system of claim 13 wherein the electric signals include respective outputs of the side arrays, and the electric signal processing means multiplies the array outputs.

15. The system of claim 11 wherein the electric signals include respective outputs of the side arrays, and the electric signal processing means multiplies the side array outputs.

16. The system of claim 11 wherein the electric signals include respective outputs of the side arrays, and the electric signal processing means adds the side array outputs.

17. The system of claim 11 wherein either the projecting means or the receiving means or both the projecting means and the receiving means are stepped from spot to spot in a random manner such that each receiving means position is paired with a projecting means position with each boundary side being fully scanned.

* * * * *